Figure 1:
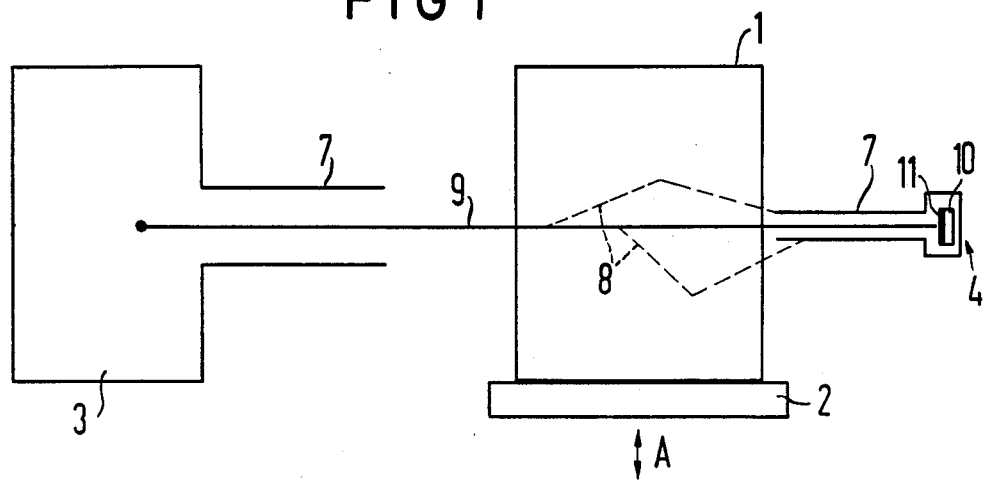

United States Patent [19]

Dönges et al.

[11] Patent Number: 4,566,113

[45] Date of Patent: Jan. 21, 1986

[54] METHOD AND APPARATUS FOR EXAMINING THE CONTENT OF CONTAINERS

[75] Inventors: Gerhard Dönges, Heidenrod-Kemel; Thomas Herwig, Eltville-Martinsthal; Claus Kunze, Taunusstein; Karl-Ulrich Stein, Munich, all of Fed. Rep. of Germany

[73] Assignee: Heimann GmbH, Wiesbaden, Fed. Rep. of Germany

[21] Appl. No.: 436,996

[22] Filed: Oct. 27, 1982

[30] Foreign Application Priority Data

Nov. 13, 1981 [DE] Fed. Rep. of Germany ....... 3145227

[51] Int. Cl.⁴ .............................................. G01N 23/04
[52] U.S. Cl. ......................................... 378/57; 378/52
[58] Field of Search ............................. 378/57, 58, 52

[56] References Cited

U.S. PATENT DOCUMENTS

| | | | |
|---|---|---|---|
| 3,594,575 | 7/1971 | Shoemaker | 378/52 |
| 4,064,440 | 12/1977 | Roder | 378/58 |
| 4,413,182 | 11/1983 | Hearn | 378/52 |
| 4,430,568 | 2/1984 | Yoshida | 378/57 |

Primary Examiner—Craig E. Church
Attorney, Agent, or Firm—Herbert L. Lerner; Laurence A. Greenberg

[57] ABSTRACT

Method for examining the content of containers, which includes weighing the container, comparing the weight of the container with a total weight derived from the net weight of a given load and the product of the volume and the packing weight of the given load, transilluminating the container with a spatially limited high energy X-ray beam, moving the container relative to the X-ray, and determining and evaluating the distribution of the mass attenuation coefficient over at least one surface of the container, and an apparatus for carrying out the method.

2 Claims, 3 Drawing Figures

METHOD AND APPARATUS FOR EXAMINING THE CONTENT OF CONTAINERS

The invention relates to a method for examining the content of containers, in which the container is weighed, and its weight is compared with the total weight from the weight of the unloaded container and the product of the volume and the packing weight of the given load.

For checking containers, such as for custom searches, the dead or net weight of the container, the volume of the container and the specific gravity or packing weight of the declared contents of the container are known.

In the examination, the total weight of the container can be determined. If this total weight is larger than if the container volume was completely filled with the declared merchandise, heavier material must be contained in the container than that which has been declared.

If the container contains lighter material than that which has been declared, this cannot be distinguished by weighing a container which is not full. In a container that is not full, heavy articles such as weapons can furthermore be hidden under lighter material, while the declared total weight of the container is adjusted so as to be correct by using a reduced filling height. In this case, no indication can be obtained regarding an undeclared or unknown container content by weighing.

It is accordingly an object of the invention to provide a method and apparatus for examining the content of containers, which overcomes the hereinafore-mentioned disadvantages of the heretoforeknown methods and devices of this general type, and to check the content of a container for articles which have not been declared without opening the container.

With the foregoing and other objects in view there is provided, in accordance with the invention, a method for examining the content of containers, which comprises weighing the container, comparing the weight of the container with a total weight derived from the net or dead weight of the container and the product of the volume and the packing weight of the declared load, transilluminating the container with a spatially limited high energy X-ray beam, moving the container relative to the X-ray, and thereby determining and evaluating the distribution of the mass attenuation coefficient over at least one surface of the container.

In this method, the mass attenuation coefficient is measured point by point by an X-ray beam with a small beam cross section. The evaluation may be in the form of a simple limitation of the mass attenuation coefficient. A more extensive evaluation is possible, however, if the measurement values are stored in a computer and the point raster resulting therefrom is reproduced, for instance, for evaluation on a monitor. In this case, an image of the content of the container is produced, the resolution of which is determined by the beam cross section.

The beam cross section in this case is made in accordance with the requirements of the resolution. High resolution requires a large number of measuring points and therefore, a large storage capacity.

In accordance with another mode of the invention, there is provided a method which comprises determining the filling height in the container from the change of the mass attenuation coefficient, determining the packing weight from the filling height and the weight of the load determined by weighing, and comparing the packing weight with the packing weight of a given container content. Thereby, the actual filling height of the container is also taken into consideration in the determination. Any measurable change of the packing weight as compared to the packing weight of the declared merchandise is recorded and prompts a more accurate examination of the container. For this embodiment of the checking process, relatively few measuring points are necessary and a small storage capacity is sufficient; the measuring process is relatively fast. The packing weight is the weight of the merchandise in the customary packing per unit volume. For loose material, it is identical with the bulk weight.

In accordance with a further mode of the invention, there is provided a method which comprises feeding the distribution of the mass attenuation coefficient over a container surface into a data memory, and evaluating spatial variations of the mass ettenuation coefficients for determining the location and nature of an undeclared unknown content in the container. The nature of the undeclared content is obtained by the extent of the article determined and the degree of the attenuation.

If only the filling height of the container is to be determined, in accordance with an added mode of the invention, there is provided a method which comprises controlling the motion of the container relative to the X-ray beam with a computer, for exclusively scanning the surface of the container contents. A particularly small number of measuring points is therefore required; the checking can be performed particularly quickly and the required storage capacity is very small.

Accurate localization of an undeclared artice in a container is made possible if, in accordance with an additional mode of the invention, there is provided a method which comprises determining the distribution of the mass attenuation coefficients for at least two different beam directions, for determining the spatial location of unknown container contents. The two beam directions may be at different angles to each other, and the disposition of the transmitter and receiver can follow considerations for mechanical construction.

For containers which are supposed to contain farm produce or fruits, the mass attenuation coefficient determined is advantageously compared with that known for water. For many cases this is already sufficient.

The determination of the density of the container contents described is based on the following relationships:

The permeability for X-rays depends exponentially on the absorption coefficient and the thickness:

$$D = e^{-\mu d},$$

where
$\mu$ = absorption coefficient, d = thickness and $\rho$ = density, which will be used below.

In X-ray physics it is customary to work with attenuation coefficients, i.e. with the quotient of the absorption coefficient divided by the density. If this value $\mu$ divided by $\rho$ is set equal to k, $d = e^{-k \cdot \rho \cdot d}$ is obtained.

For k, the value for water can be substituted as a constant. The thickness of the transilluminated layer can be set equal to the thickness of the container and can therefore likewise be considered as a constant. Accordingly, the permeability for X-rays still depends in sufficient approximation only on the density of the material between the two container walls. These relationships apply in the present simple form for a given energy of the X-rays, For the mixed radiation of an X-ray generator, a value which is integrated over the entire spectrum is substituted for k.

In a further embodiment of the method, a vapor sample is taken from the container; the vapor sample is analyzed in a mass spectrometer and from this analysis and the measurements of the density and the density distribution, the nature of the undeclared contents of the container is determined.

By determining gun powder residue, in particular, used weapons can be distinguished from other metal articles. Weapon oil is also noticed in the mass spectroscopy analysis and indicates oiled weapons.

Scanning of the container by rows or columns is achieved if, in accordance with again another mode of the invention, there is provided a method which comprises pushing the container in a back and forth motion and in an up and down motion, one of the motions being continuous and the other of the motions being stepwise, carrying out one of the transillumination and evalution steps pulsewise, and setting the pulses short enough to prevent unpermissible or excessive motion blurs from entering into the measured values. In this manner, a very high passage velocity can advantageously be achieved, since the heavy container is moved uniformly in one direction but not step by step. Only after its entire length is traversed is it advanced by one step in the second direction. In this method, every point of the container is covered in spite of a high operating speed. A sufficiently accurate examination of a container is possible with this process in about 10 minutes. It is then possible to let either the radiation source or the receiver work continuously while the respective other part operates pulsewise.

The method according to the invention is advantageously performed in an apparatus for examining the contents of containers, comprising a container having walls for holding objects therein, a lifting platform for supporting the container and for moving the container at least vertically in height and in a plane direction through a given range of motion of the container walls, at least one stationary X-ray source disposed on one side of the lifting platform beyond the given range of motion of the container walls emitting a main beam and producing scatter radiation from transilluminated objects in the container, a stationary X-ray radiation receiver disposed on another side of the lifting platform opposite the one side beyond the given range of motion of the container walls, the main beam from the X-ray source striking the X-ray receiver and the scatter radiation from the transilluminated objects being unable to reach the receiver.

In accordance with again a further feature of the invention, the X-ray receiver includes a scintillation crystal emitting radiation and an opto-electric converter for receiving the radiation emitted by the scintillator crystal, the opto-electric converter having an output connectible to a computer suitable for storing signals. The scintillation crystal in this case accepts only a beam cross section which corresponds to its size. It therefore defines the resolution of the apparatus. Light-emitting diodes or photo multipliers are suitable as opto-electric converters. In order to eliminate stray radiation with certainty, it is advantageous to place a collimator both at the output of the radiation source and ahead of the receiver. The collimator allows only approximately parallel radiation to leave the radiation source and to enter the receiver.

A rather simple ambodiment of the apparatus is obtained if it contains a hydraulic lifting and pushing mechanism which can move the lifting platform back and forth or up and down in such a way that the containers are scanned row by row or column by column. The container is advantageously moved continuously in the longitudinal direction while the lifting motion is step by step. Thus, the container is moved continuously in its largest dimension, and the height of the container which is to be scanned step by step is substantially smaller than its length.

Thus, in accordance with again an added feature of the invention, the X-ray source emits divergent main beams scanning the container in a given direction, the X-ray receiver includes a plurality of scintillation crystals disposed in a row for separating the divergent beams and for emitting radiation and a separate opto-electric converter each receiving the radiation emitted by a respective one of the scintillation crystals, the scintillation crystals being disposed along a direction different from the given scanning direction, and line by line feeding means for advancing the container in a given feed direction from one line to another line after a line has been scanned, for adjusting a feed to a value corresponding to the overall dimension of the main beams received by the scintillation crystals in the given feed direction, as measured at the entrance of the main beams into the container.

Furthermore, in accordance with a concomitant mode of the invention, there is provided a method which comprises scanning the container line by line in a given direction, transilluminating the container with at least one divergent X-ray beam during scanning, measuring the distribution of the attenuation coefficient with the divergent X-ray beam at a plurality of individual measuring points being offset relative to each other in direction perpendicular to the given scanning direction, storing measurement values obtained in this manner in scanning a line as measurement strips, and completely calculating the spatial location of an object in the container from the line spacing and the beam directions at the individual measuring points, from the location of an unknown object in at least two of the measuring strips.

Other features which are considered as characteristic for the invention are set forth in the appended claims.

Although the invention is illustrated and described herein as embodied in a method and apparatus for examining the content of containers, it is nevertheless not intended to be limited to the details shown, since various modifications and structural changes may be made therein without departing from the spirit of the invention and within the scope and range of equivalents of the claims.

Figure 2:
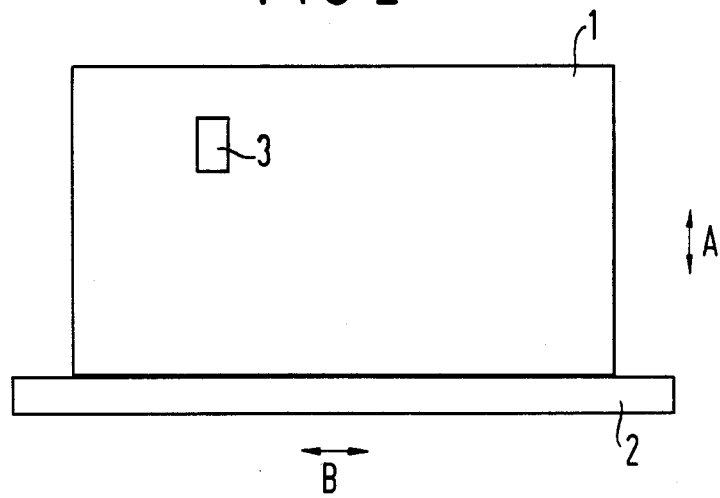
Figure 3:
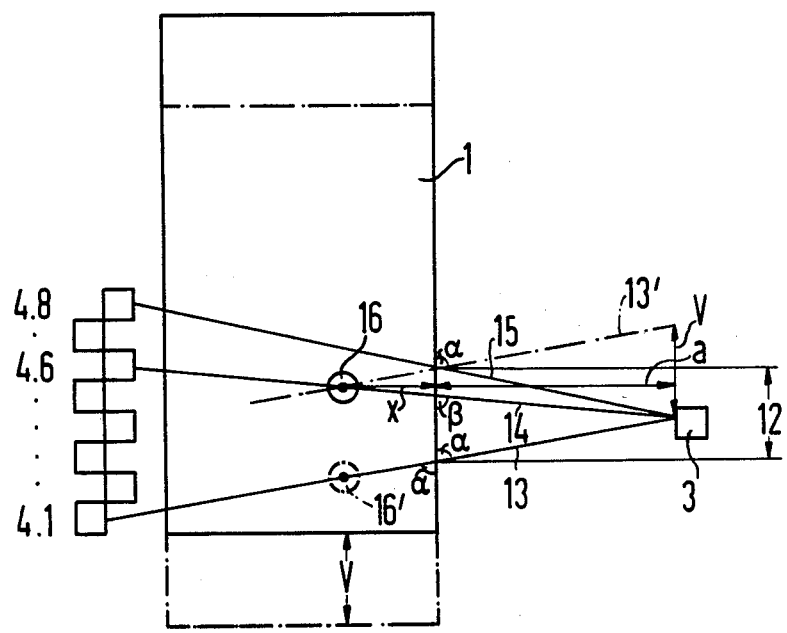

The construction and method of operation of the invention, however, together with additional objects and advantages thereof will be best understood from the following description of specific embodiments when read in connection with the accompanying drawings, in which:

FIGS. 1 and 2 are diagrammatic elevational views of an apparatus according to the invention, as seen from two different directions; and FIG. 3 is a view of a further embodiment of the invention.

Referring now to the figures of the drawing and first particularly to FIGS. 1 and 2 thereof, it is seen that a container 1 lies on a lifting platform 2. An X-ray generator 3 emits an X-ray 9 through the container 1 to a receiver 4. The receiver 4 has a scintillation crystal 11. The light emitted by the scintillation crystal is fed to a photo-electric converter 10. At the radiation outlet of the X-ray generator 3 and upstream of the inlet of the detector 4, respective collimators 7 are disposed. Only an approximately parallel beam can pass through the collimators 7. Scatter or stray light in the X-ray source is field-limited or masked in the same way as stray rays 8 which are generated by scattering in the container, and are reflected to the receiver 4.

The X-ray generator 3 and the receiver 4 are stationarily mounted and are accurately adjusted. The lifting platform 2 with the container 1 is moved in directions A and B. Preferably, the movement in the direction B is continuous and permits scanning line by line, and the movement is a step-by-step motion in the direction A after each passage in the direction B. The step-by-step motion in the direction A can take place at every reversal point of the motion of the container in the direction B. Advantageously, either the X-ray generator 3 or the receiver 4 is switched on pulse-wise during the movement of the container in the direction B, so that the measurement of the mass attenuation coefficient is performed in such a short time interval that no interfering motion blur enters into the measurement values.

The measuring speed can be increased by constructing the device according to an embodiment in which the receiver is in the form of several scintillation crystals disposed in a row and a separate opto-electrical converter for each scintillation crystal, which can be reached or impinged by the radiation of the crystal; all scintillation crystals can be reached by the X-ray of the X-ray source; and the signal output of each individual opto-electric converter is fed to a computer suitable for storing the signals. The X-ray may be a parallel beam, the dimensions of which cover all scintillation crystals. The X-ray may also be a divergent beam which then must have a suitable dimension only on the side of the receivers so as to cover all scintillation crystals. Each scintillation crystal limits a main beam in this case; scattered light is blanked out. The X-ray beam may also be composed of several main beams which have already become parallel in the X-ray source and which are always directed toward a scintillation crystal.

Localization in space of an object in the container is made possible by an embodiment of the invention in which the X-ray source emits divergent main beams; several scintillation crystals disposed in a row are provided as receivers, and a separate opto-electric converter is provided for each scintillation crystal, which can be reached by the radiation of the crystal, where the scintillation crystals delineate or separate the divergent main beams; the scintillation crystals are distributed in a direction different from the scanning direction; and a feed device which advances to the next line after one line is scanned, permits adjustment of the feed to a value which corresponds overall to the extent of the main beams covered by the scintillation crystals in the feed direction, as measured at the entrance into the container. The determination of the position in space of the object is possible in this case by simple trigonometric calculations or even graphically. If according to FIG. 3, for instance, an object 16 is indicated in a first measuring strip by a main beam 15 at a measuring point 4.6, and in a second measuring strip by a main beam 13 at a measuring point 4.1, a distance x from the container wall is obtained from the feed V between the two measurements, angles $\alpha$ and $\beta$ between the rays and the container wall, and a distance "a" between the container wall and the X-ray generator 3:

$$(a+x)\tan\alpha + (a+x)\tan\beta = V$$

and from this, after transformation $$x = V/(\tan\alpha + \tan\beta) - a$$

where $\tan\alpha$ and $\tan\beta$ are constants of the equipment and for each correlation of two main beams, a value for $\tan\alpha + \tan\beta$ can be stored. In order to illustrate the relationship of the shift of the container by the displacement V, the main beam 13 has been shown as offset by the displacement V in a position 13'. When using the hereinafore-mentioned method, every point of an object in the container can be localized, and thus the size of the article can also be determined and its volume and its specific gravity can be calculated.

The displacement V need not correspond to the feed for one line spacing. The feed per line, however, must not be larger than a total dimension 12 over all main beams on the container side which is facing the X-ray generator 3. It is thus ensured that each point of the container will be transilluminated. If the feed is chosen not larger than one-half of the total dimension 12, then every point is covered in at least two measuring strips and can therefore be localized in space.

A natural radioactive radiator is advantageously used as the X-ray source for small containers and loads with small mass attenuation coefficients. For universal systems which are also to examine loads with high mass attenuation coefficients, an X-ray generator for X-rays of about 1 MeV to 20 MeV is advantageous.

We claim:

1. Method for examining the content of containers, which comprises weighing the container, comparing the weight of the container with a total weight derived from the weight of the unloaded container and the product of the volume and the packing weight of a declared load, transilluminating the container with a spatially limited high energy X-ray beam, moving the container relative to the X-ray beam so as to scan one surface of the container from at least two different directions, determining and evaluating the distribution of the mass attenuation coefficient of the contents of the container along said two directions determining the filling height in the container from the change of the mass attenuation coefficient, determining the packing weight from the filling height and the weight of the load determined by weighing, comparing the packing weight with the packing weight of the declared container content and determining the spatial location of unknown container contents from the mass attenuation coefficients along said two directions.

2. Method according to claim 1 which comprises scanning the container line by line in a given direction, transilluminating the container with at least one divergent X-ray beam during scanning, measuring the distribution of the attenuation coefficient with the divergent X-ray beam at a plurality of individual measuring points being offset relative to each other in direction perpendicular to the given scanning direction, storing measurement values obtained in scanning a line as measurement strips, and calculating the spatial location of an object in the container fom the line spacing and the beam directions at the individual measuring points, from the location of an unknown object in at least two of said measuring strips.

* * * * *